US012796925B2

(12) United States Patent
Bozchalooi et al.

(10) Patent No.: US 12,796,925 B2
(45) Date of Patent: Nov. 17, 2026

(54) HEAD-MOUNTED DEVICE INCLUDING DISPLAY FOR FULLY-AUTOMATED OPHTHALMIC IMAGING

(71) Applicant: The Regents of the University of California, Oakland, CA (US)

(72) Inventors: Iman Soltani Bozchalooi, Sacramento, CA (US); Parisa Emami-Naeini, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 295 days.

(21) Appl. No.: 18/550,897

(22) PCT Filed: Apr. 11, 2022

(86) PCT No.: PCT/US2022/024304
§ 371 (c)(1),
(2) Date: Sep. 15, 2023

(87) PCT Pub. No.: WO2022/217160
PCT Pub. Date: Oct. 13, 2022

(65) Prior Publication Data

US 2024/0237897 A1 Jul. 18, 2024

Related U.S. Application Data

(60) Provisional application No. 63/173,009, filed on Apr. 9, 2021.

(51) Int. Cl.
*A61B 3/18* (2006.01)
*A61B 3/00* (2006.01)
(Continued)

(52) U.S. Cl.
CPC ................ *A61B 3/18* (2013.01); *A61B 3/005* (2013.01); *A61B 3/102* (2013.01); *A61B 3/113* (2013.01);
(Continued)

(58) Field of Classification Search
CPC ........... A61B 3/18; A61B 3/005; A61B 3/102; A61B 3/113; A61B 3/12; A61B 3/152;
(Continued)

(56) References Cited

U.S. PATENT DOCUMENTS

2015/0351631 A1 12/2015 Narasimha-Iyer et al.
2016/0270656 A1 * 9/2016 Samec ................ A61B 5/1455
(Continued)

FOREIGN PATENT DOCUMENTS

CN 111084605 A * 5/2020 .............. A61B 3/14

OTHER PUBLICATIONS

English translation of CN111084605 (May 1, 2020).*

*Primary Examiner* — William R Alexander
*Assistant Examiner* — Kuei-Jen L Edenfield
(74) *Attorney, Agent, or Firm* — Byrne Poh LLP

(57) ABSTRACT

This disclosure provides a wearable device implemented as a headset such as a virtual reality (VR) headset comprising at least a screen, a gaze tracker, and either one or both the anterior segment or retinal optical coherence tomography and fundus imaging modalities. In some embodiments, the disclosed headset can display a movie on the screen to catch/hold the attention of a patient, and meanwhile capture ocular images of the patient using the ophthalmic imaging modalities in a fully-automated manner. While capturing ophthalmic images, the movie on the screen can cause the patient's gaze to move in various directions in a controllable manner. The gaze tracker can track the movements of the pupils of the patient. The tracked pupil positions can be used
(Continued)

to reposition the ophthalmic imaging modalities to refocus and capture images of different regions of the fundus/retina, which allows a widefield-of-view image of the fundus/retina to be reconstructed.

33 Claims, 5 Drawing Sheets

(51) Int. Cl.

| | |
|---|---|
| ***A61B 3/10*** | (2006.01) |
| ***A61B 3/113*** | (2006.01) |
| ***A61B 3/12*** | (2006.01) |
| ***A61B 3/15*** | (2006.01) |
| ***G02B 27/01*** | (2006.01) |

(52) U.S. Cl.
CPC ................ *A61B 3/12* (2013.01); *A61B 3/152* (2013.01); *G02B 27/0172* (2013.01)

(58) Field of Classification Search
CPC .... A61B 3/00; A61B 3/10; A61B 3/15; G02B 27/0172; G02B 27/0093; G02B 27/01; G02B 27/00; G06F 3/013; G06F 3/01
USPC .................................................. 351/206–211
See application file for complete search history.

(56) References Cited

U.S. PATENT DOCUMENTS

| | | | |
|---|---|---|---|
| 2017/0014026 A1 | 1/2017 | Guyton et al. | |
| 2018/0084232 A1 | 3/2018 | Belenkii et al. | |
| 2019/0046124 A1 | 2/2019 | Samadani | |
| 2019/0090733 A1 | 3/2019 | Walsh et al. | |
| 2020/0093361 A1* | 3/2020 | Jackson ............. | G02B 27/0176 |
| 2022/0151489 A1* | 5/2022 | Khan ..................... | A61B 3/102 |

* cited by examiner

HEAD-MOUNTED DEVICE INCLUDING DISPLAY FOR FULLY-AUTOMATED OPHTHALMIC IMAGING

CROSS-REFERENCE TO RELATED APPLICATION

This application claims the benefit of U.S. Provisional Patent Application Ser. No. 63/173,009, entitled "Head Mounted Device Including Stereoscopic Display and Optical Imaging and/or Sensing Modalities,", filed on 9 Apr. 2021, the contents of which are incorporated by reference herein.

BACKGROUND

Field

The disclosed embodiments generally relate to medical imaging devices and systems. More specifically, the disclosed embodiments relate to a head-mounted wearable device that includes one or more ophthalmic imaging modalities for fully automated ocular imaging.

Related Art

Ophthalmic imaging modalities such as optical coherence tomography (OCT) and fundus imaging have been widely used in eye clinics for the diagnosis and follow-up of patients with various ophthalmic conditions, and have become the mainstay of diagnosis in these patients. OCT renders cross-sectional scans of the retina and the anterior segment of the eye. Both OCT and fundus imaging are non-invasive and relatively easy to perform on a cooperative patient.

In addition to patient cooperation, these ophthalmic imaging modalities further require the patient to be present at an ophthalmology clinic or capable of making simple adjustments to portable versions of the device. These seemingly simple requirements, however, can be very difficult in patients with mental disability or other medical conditions such as physical disabilities, and also for patients that are very young children. In fact, in children and patients with mental disability, OCT and fundus imaging can be nearly impossible to perform due to lack of cooperation by the patients. This often results in misdiagnosis and underdiagnosis of blinding conditions in these vulnerable patient groups.

Hence, what is needed is an ophthalmic imaging system and technique including one or multiple ophthalmic imaging modalities without the drawbacks of the existing systems and techniques.

SUMMARY

This disclosure provides a wearable device implemented as a headset such as a virtual reality (VR) headset comprising at least a screen, a gaze tracker, and either one or both the anterior segment or retinal optical coherence tomography and fundus imaging modalities. In some embodiments, the disclosed headset can display images, movies or animations on the screen to catch and hold the attention of an otherwise uncooperative patient, and at the same time capture ocular images of the patient using one or both ophthalmic imaging modalities in a fully automated manner. While capturing ophthalmic images, the images on the screen cause the patient's gaze to move in various directions in a controllable manner. The gaze tracker in the disclosed headset tracks the movements of one or both pupils of the patient viewing the screen. The tracked pupil positions (in 2D or 3D) can be used to reposition the optics associated with one or both of the ophthalmic imaging modalities to focus and capture images of different regions of the fundus/retina, which allows a wide field-of-view image of the fundus/retina to be reconstructed.

Because the disclosed ophthalmic imaging techniques are fully automatic, the need for patient cooperation to acquire ophthalmic images is completely removed. The disclosed ophthalmic imaging process can also turn an otherwise unpleasant eye examination process into a pleasant one that allows very young children or those with mental challenges such as autism to benefit from these imaging technologies. The simplified and fully automated imaging process also makes it possible for patients to receive more frequent imaging procedures for enhanced disease management. Moreover, because the disclosed ophthalmic imaging systems and techniques can obviate the need for technicians and other clinical resources, the imaging costs can be significantly reduced to allow the disclosed ophthalmic imaging technology to be accessible to a wider range of patient groups. By incorporating ophthalmic imaging functions into a portable and wearable system, the disclosed ophthalmic imaging headsets offer various opportunities in the realm of tele-medicine/health, wherein the disclosed devices can be used by patients in the convenience of their own homes.

In one aspect, a wearable eye examination device is disclosed. This wearable eye examination device can include one or more ophthalmic imaging modalities for obtaining one or more forms of ophthalmic information of a user wearing the wearable device. The wearable device also includes a screen to display a video to the user wearing the wearable device. The wearable device additionally includes a gaze tracker configured to track positions of a pupil of the user viewing the screen. The wearable device further includes an optical adjustment module configured to align a region of the user's eye with the one or more ophthalmic imaging modalities based on a determined position of the pupil.

In some embodiments, the one or more ophthalmic imaging modalities include at least an optical coherence tomography (OCT) and a fundus imaging module.

In some embodiments, the screen, when displaying the video, acts as an illumination source for the one or more ophthalmic imaging modalities.

In some embodiments, the gaze tracker further includes a camera for capturing one or more real-time images of the pupil, and a processing module configured to determine a position of the pupil based on the captured real-time images of the pupil.

In some embodiments, the optical adjustment module further includes a processing module configured to covert the position of the pupil into an actuation signal In some embodiments, the optical adjustment module further includes one or more actuated optical components coupled between the position of the user's eye and the ophthalmic imaging modalities. Moreover, the optical adjustment module is configured to align the region of the user's eye with the one or more ophthalmic imaging modalities by repositioning the one or more actuated optical components based on the actuation signal so that the reflected light from the region of the user's eye is aligned with optical axes of the one or more ophthalmic imaging modalities.

In some embodiments, the one or more actuated optical components include one or both of an actuated beam splitter and an actuated mirror.

In some embodiments, the actuated beam splitter is positioned between the user's eye and the screen and is configured to transmit a first portion of the incident light toward the user's eye and reflect a second portion of the incident light toward the actuated mirror.

In some embodiments, the processing module is further configured to: (1) determine the completion of the repositioning of the one or more actuated optical components; and (2) generate an imaging instruction to the one or more ophthalmic imaging modalities.

In some embodiments, the one or more ophthalmic imaging modalities, upon receiving the imaging instruction, are further configured to capture both OCT scans and fundus images of the region of the user's eye.

In some embodiments, the region of the user's eye includes a central region of the retina and a peripheral region of the retina.

In some embodiments, the wearable device further includes an image processing module configured to reconstruct widefield OCT scans and fundus images including both central and peripheral retina regions of the patient's eye based on captured OCT scans and fundus images from different regions of the user's eye during an extended ophthalmic imaging period.

In some embodiments, the wearable device is implemented as a virtual reality (VR) headset.

In some embodiments, the wearable device allows for performing ophthalmic imaging on the user over an extended examination period facilitated by the relaxing and entertaining content of the displayed video and the comfort of the user wearing the headset.

In some embodiments, the extended examination period facilitates the capture of multiple OCT scans and fundus images of each region of the user's eye to improve image qualities of the ophthalmic imaging.

In some embodiments, the wearable device enables fully-automatic ophthalmic imaging without involving a technician.

In some embodiments, the wearable device is implemented as an OCT-fundus dual modality headset.

In some embodiments, the wearable device enables fully-automatic ophthalmic imaging without requiring the user's cooperation.

In another aspect, a process of performing a fully-automatic ophthalmic imaging procedure is disclosed. This process can begin by displaying a video on a screen to guide a patient's eye to a new location on the screen. The process then determines a real-time position of the patient's pupil. Next, the process converts the real-time position of the patient's pupil into a control signal to cause one or more ophthalmic imaging modalities to realign with a new retinal region of the patient's eye. The process subsequently captures ophthalmic images of the new retinal region using the one or more ophthalmic imaging modalities.

In some embodiments, the one or more ophthalmic imaging modalities include at least an optical coherence tomography (OCT) and a fundus imaging module.

In some embodiments, the process determines the real-time position of the patient's pupil by capturing one or more real-time images of the patient's pupil and determining the position of the patient's pupil based on the captured real-time images.

In some embodiments, the process determines the real-time position of the patient's pupil using a gaze tracker.

In some embodiments, the process causes the one or more ophthalmic imaging modalities to realign with a new retinal region of the patient's eye by repositioning one or more optical components disposed between the patient's eye and the one or more ophthalmic imaging modalities so that the reflected light from the new retinal region of the patient's eye is aligned with optical axes of the one or more ophthalmic imaging modalities.

In some embodiments, prior to capturing the ophthalmic images, the process further includes the steps of: (1) determining the completion of the repositioning of the one or more actuated optical components; and (2) generating an imaging instruction to the one or more ophthalmic imaging modalities to trigger imaging functions of the one or more ophthalmic imaging modalities.

In some embodiments, the process extends a duration of the ophthalmic imaging procedure by displaying relaxing and entertaining content on the screen.

In some embodiments, the ophthalmic imaging procedure is performed without involving a technician.

In some embodiments, the ophthalmic imaging procedure is performed without requiring the patient's cooperation.

In some embodiments, the ophthalmic imaging procedure is performed at a patient's home.

In yet another aspect, an ophthalmic imaging headset is disclosed. This ophthalmic imaging headset includes one or more ophthalmic imaging modalities for obtaining one or more forms of ophthalmic information of a user wearing the headset. The ophthalmic imaging headset also includes a screen for displaying a video to the user wearing the headset to catch and hold the user's attention to one or more locations on the screen. The ophthalmic imaging headset additionally includes an optical adjustment module configured to maintain optical access of the one or more ophthalmic imaging modalities to one or more regions of interest of one or both eyes of the user.

In some embodiments, the one or more ophthalmic imaging modalities include at least an optical coherence tomography (OCT) for capturing posterior segment images of one or both eyes of the user and a fundus imaging module for capturing retinal images of one or both eyes.

In some embodiments, the ophthalmic imaging headset further includes a gaze tracker for tracking and determining positions of one or both pupils of one or both eyes.

In some embodiments, the optical adjustment module is configured to maintain the optical access of the ophthalmic imaging modalities to the one or more regions of interest of one or both eyes of the user based on the determined positions of one or both pupils.

In some embodiments, the optical adjustment module includes one or both of an actuated beam splitter and an actuated mirror.

In some embodiments, the optical adjustment module includes a stationary beam splitter.

DETAILED DESCRIPTION

Figure 1:
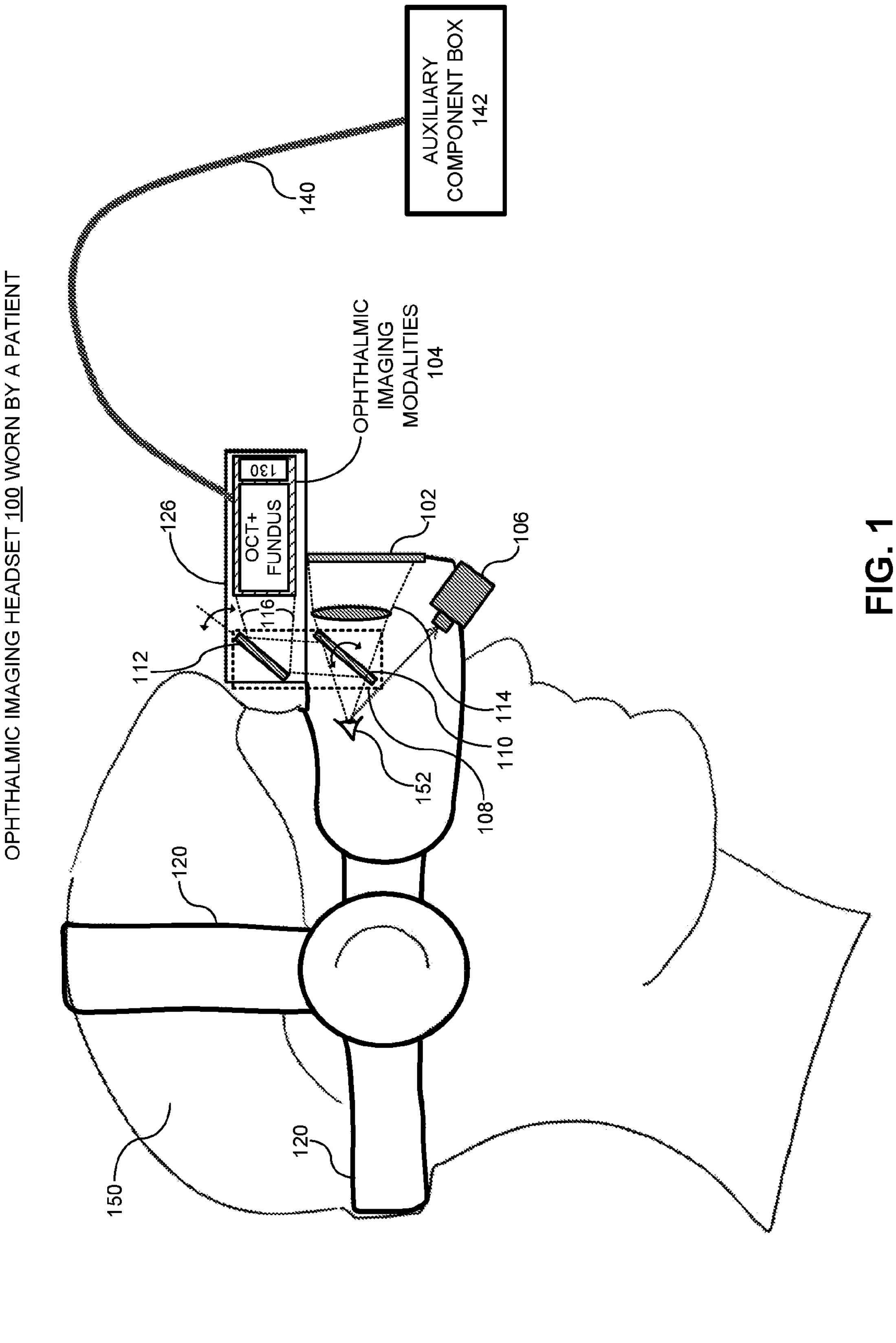
FIG. 1 shows a high-level schematic of the proposed wearable ophthalmic imaging device in accordance with the disclosed embodiments.

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, microprocessors, application-specific integrated circuit (ASIC) chips, field-programmable gate arrays (FPGAs), and other programmable-logic devices now known or later developed. When the hardware modules are activated, the hardware modules perform the methods and processes included within the hardware modules.

This disclosure provides a wearable device in the form of a headset configured to be worn over the head and eyes of a user or patient (the terms "user" and "patient" are used interchangeably below). The headset includes at least (1) a screen that provides animations and/or videos to the user, (2) an eye/gaze tracker configured to track the user/patient's gaze as he/she watches animations and/or videos displayed on the screen, (3) one or more fully-automated ophthalmic imaging mechanisms for capturing one or both anterior segment and retinal/fundus images of the user/patient's eyes, and (4) an optical adjustment module that is configured to automatically reposition/refocus the ophthalmic imaging mechanisms to focus and capture images of various regions of the fundus (including both central and peripheral retina) based on the detected movements of the patient's gaze.

Note that the headset stores videos/animations that, when displayed on the screen for a predetermined period of time during an imaging procedure, cause the user/patient's gaze to move in different directions away from the center of the screen. Such movements in conjunction with the eye/gaze tracker and the optical adjustment system enable a fundus imaging mechanism to capture multiple images of both central and peripheral portions of the retina, thereby allowing a wide field image of the fundus to be reconstructed by combining the many images. By presenting an entertaining video to the user/patient in a relaxed manner (both in terms of the displayed content and the comfort of the headset), an extended imaging/examination duration greater than a minimal required examination time can be easily achieved and, over time, detailed images of various parts of the eyes are seamlessly captured.

The disclosed wearable device/headset finds use in a variety of settings, including primary care/pediatrician locations, optometrist offices, drugstores and the private homes of the patients.

FIG. 1 shows a high-level schematic of the disclosed head-mounted ophthalmic imaging device 100 (which is worn on a patient's head 150) in accordance with the disclosed embodiments. As can be seen in FIG. 1, the disclosed head-mounted ophthalmic imaging device/headset 100 (or "head-mounted imaging device 100," "ophthalmic imaging headset 100," or simply "headset 100" hereinafter) includes straps 120 that allow ophthalmic imaging headset 100 to be comfortably worn on the patient's head 150. Note that the disclosed ophthalmic imaging headset 100 also includes a screen 102 positioned directly in front of the eyes 152 (only one eye is explicitly shown) of the patient's head 150. In various embodiments, ophthalmic imaging headset 100 can be configured to display either two-dimensional (2D) videos or three-dimensional (3D) videos on screen 102. In various embodiments, ophthalmic imaging headset 100 can also be configured to display a sequence of still images on screen 102. In specific embodiments, ophthalmic imaging headset 100 can be configured as a virtual reality (VR) headset to display fully immersive 3D animations or videos on screen 102.

In some embodiments, light emitted from screen 102 can be used as a light source to illuminate both the anterior segment and retinal/fundus of the patient's eyes 152, so that the ophthalmic images can be captured by the ophthalmic imaging modalities of the ophthalmic imaging headset 100. In other embodiments, an additional light source separate from screen 102 (e.g., a light source integrated with the ophthalmic imaging modalities) can be used in conjunction with the emitted light from screen 102 to provide stronger illumination on both the anterior segment and retinal/fundus of the patient's eyes 152.

In some embodiments, screen 102 can comprise a smartphone for displaying the videos/animations/images. In these embodiments, the smartphone itself can be coupled to various modules of the ophthalmic imaging headset 100, including the eye/gaze tracker and the ophthalmic imaging modalities, to conduct part of the necessary data processing such as determining pupil positions and some simple ocular health evaluations. This means that some of the hardware and software of the ophthalmic imaging headset 100 can be migrated onto the smartphone, thereby reducing instrument costs. Using the smartphone as screen 102 can also enable direct access to the internet for tele-ophthalmology and/or cloud computing functionalities, including machine learning-based or other post data acquisition processing. This real-time computation capability facilitates timely diagnosis and treatment planning, which leads to additional healthcare cost savings.

Note that the disclosed ophthalmic imaging headset 100 also includes ophthalmic imaging modalities 104 for capturing both anterior and retinal/fundus segments of the patient's eyes 152. In some embodiments, ophthalmic imaging modalities 104 can include an integrated OCT and fundus imaging setup. In the exemplary headset 100 shown in FIG. 1, ophthalmic imaging modalities 104 are positioned directly above screen 102 inside a housing 126. In some embodiments, ophthalmic imaging modalities 104 can include an optical coherence tomography (OCT) module and a fundus/retinal imaging module placed side-by-side and configured to either simultaneously or separately capture OCT scans of the anterior segments of the eyes and fundus images of the retinas of the eyes 152. In these embodiments, each of the separate OCT module and fundus imaging module can include a separate sensing hardware or camera. Note that ophthalmic imaging modalities 104 can include a light source 130, such as a laser source or an LED light for illuminating the corneas and fundus of the patient's eyes 152 to facilitate capturing OCT scans and fundus images of the patient's eyes 152. Note that the illumination from light source 130 can be used to strengthen the illumination from screen 102.

In some other embodiments, ophthalmic imaging modalities 104 can include an integrated OCT and fundus imaging module that is configured to simultaneously capture OCT scans of the posterior segment of the eyes 152 and fundus images of the retina. In these embodiments, the OCT module and the fundus imaging module of the integrated OCT-fundus module share certain optical elements. In some other embodiments, ophthalmic imaging modalities 104 include at least one of an OCT module and a fundus imaging module, and at least one other ocular test component, such as an OCT angiography, a fluorescein angiography, scanning laser ophthalmoscopy, intraocular pressure sensor, indocyanine green angiography, a visual field test (i.e., perimetry), a visual acuity test, an autorefractor, a corneal topography, and an optical biometry.

To avoid increasing the weight of headset 100, an optical fiber/wire bundle 140 can be used to place certain auxiliary electronic, optical, or memory components in a non-cloud-based location, such as within an auxiliary component box 142 that is separate from headset 100. Alternatively, headset 100 can be wirelessly connected to auxiliary component box 142 without using fiber/wire bundle 140. It will be understood by one of skill in the art that various processing, imaging, diagnostic equipment, or any combinations thereof can be housed in auxiliary component box 142.

Note that an important advantage of the disclosed ophthalmic imaging headset 100 is that the ophthalmic imaging operations are independent from the body and head motions of the patients, because such movements are automatically accommodated by the fact that the imaging headset 100 is firmly attached to the patient's head (e.g., by means of straps 120) and hence moves in tandem with the patient's body and head. As such, to realign the patient's eyes 152 with ophthalmic imaging modalities 104, only the globe motion/rotation (of the patient's eyes 152) and associated pupil movements need to be determined and compensated using the fully-automated optical adjustment module 108 (described below) while the patient watches the video. In contrast, the ability to accommodate body and head movements is particularly challenging for existing hand-held OCT systems and devices.

The disclosed ophthalmic imaging headset 100 further includes eye/gaze tracker 106, which is configured to track the patient's gaze as he/she watches a video displayed on screen 102. Specifically, gaze tracker 106 can include a camera for taking high resolution images of one or both of the patient's eyes 152 including one or both pupils and corneas, an illuminator configured to project certain patterns onto the eyes, and a processing module (i.e., one or more integrated circuit (IC) chips containing programs) configured to determine one or more dynamic and real-time positions of the pupil(s) due to the changes to the patient's gaze as the patient watches the video during an ophthalmic imaging period.

As can be seen in FIG. 1, the disclosed ophthalmic imaging headset 100 further includes an optical adjustment module 108 coupled to gaze tracker 106 and configured to automatically realign ophthalmic imaging modalities 104 to maintain optical access to different regions of the fundus (including both central and peripheral retina) based on the detected positions of one or both pupils due to movements of the patient's gaze. In the embodiment shown, optical adjustment module 108 can include an actuated beam splitter 110 and an actuated mirror 112. While not explicitly shown, optical adjustment module 108 also includes actuation mechanisms for each of the actuated beam splitter 110 and actuated mirror 112, wherein each of the actuation mechanisms can be directly attached to the associated optical component, and control circuits which are coupled to the actuated optical components 110 and 112 and are configured to convert the pupil tracking outputs from gaze tracker 106 into actuation signals for the associated actuation mechanism.

Note that actuated beam splitter 110 has two functions. First, actuated beam splitter 110 is positioned between patient's eyes 152 and screen 102, and is configured to provide visual access to screen 102 through the transmitted light 114. Second, actuated beam splitter 110 (in conjunction with actuated mirror 112) guides illustration light from the light source 130 in ophthalmic imaging modalities 104 to the current locations of the pupils of the patient's eyes 152 and, at the same time, guides reflected light 116 from the current locations of the pupils of the patient's eyes 152 toward ophthalmic imaging modalities 104.

Moreover, actuated beam splitter 110 and actuated mirror 112 are configured to receive real-time positions of the pupils generated by gaze tracker 106, adjust their positions to guide the illumination light toward the newly determined positions of the pupils, and guide the reflected light 116 from different peripheral locations of the retina toward ophthalmic imaging modalities 104.

A person skilled in the art can readily appreciate that the repositioning and realignment operations of the disclosed optical adjustment module 108 are fully automatic and fast, and may be facilitated by high-speed actuators (not shown) attached to actuated beam splitter 110 and actuated mirror 112. In various embodiments, optical adjustment module 108 is compact in order to achieve high actuation speed.

Moreover, it is preferable that actuated beam splitter 110 and actuated mirror 112 have a large adjustment range to accommodate a full range of pupil motion when the patient watches the video on screen 102. It should also be readily understood by a person skilled in the art that in other embodiments the same optical realignment objective achieved by optical adjustment module 108 can be achieved via other arrangements of optical elements, e.g., by using a stationary beam splitter or mirror while moving other optical components within the optical path between eyes 152 and ophthalmic imaging modalities 104.

However, a trade-off generally exists between the imaging/adjustment range and overall imaging speed and quality. As such, depending on the application, optical adjustment module 108 can be configured to limit the optical adjustment range to achieve a higher image quality. This can be achieved by limiting the range of the pupil movement by selecting a video from a library of videos such that most of the activities in the selected video occur near the central region of screen 102.

Figure 2B:
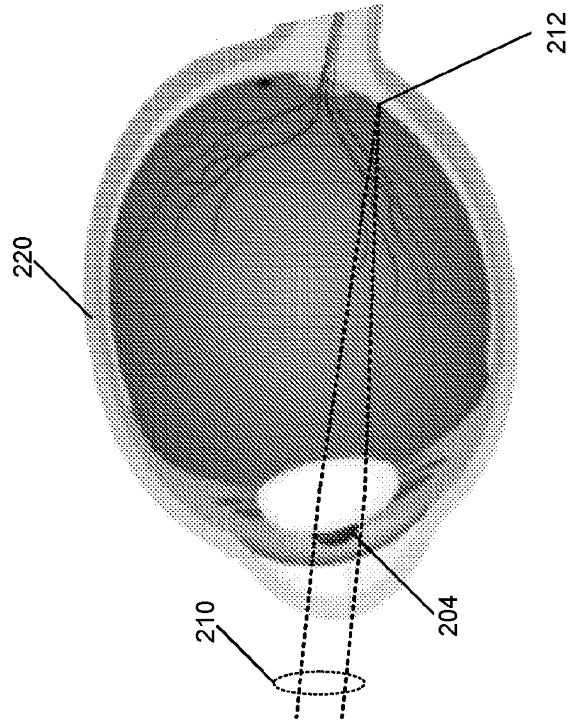
FIG. 2B shows an exemplary process of aligning the ophthalmic imaging components with a peripheral retina region of the fundus in accordance with the disclosed embodiments.
Figure 2A:
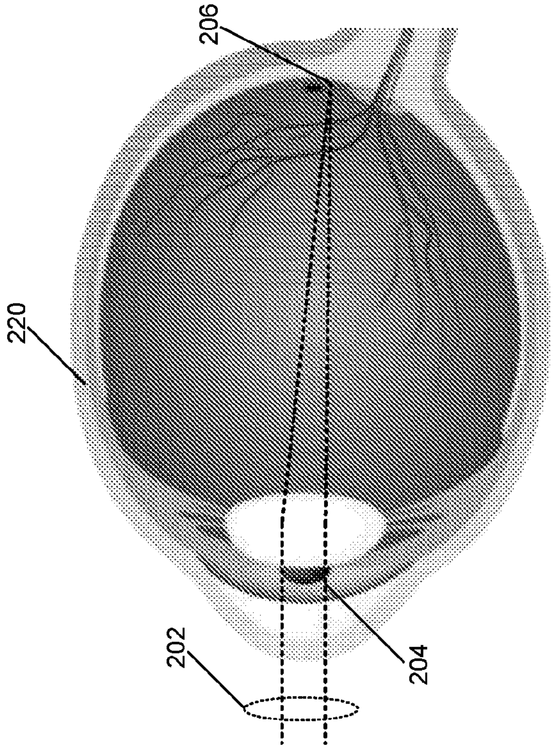
FIG. 2A shows an exemplary process of aligning the ophthalmic imaging components with the central retina region of the fundus in accordance with the disclosed embodiments.

Note that the disclosed ophthalmic imaging process and technique facilitate generation of widefield or ultra-widefield ocular images that include both central and peripheral retina of the eyes 152. Such widefield or ultra-widefield ocular images are made possible by presenting entertaining videos/VR games to the patient to guide the patient's gaze to different directions away from the center of the screen. By guiding the patient's gaze to different locations on screen 102, the optical adjustment module 108 allows the ophthalmic imaging modalities 104 to access various regions of the retina. FIGS. 2A and 2B collectively illustrate the concept of accessing different regions of the fundus using the disclosed ophthalmic imaging headset 100 in accordance with the disclosed embodiments. Specifically, FIG. 2A shows an exemplary process of aligning the ophthalmic imaging modalities 104 with the central retina region of the fundus in accordance with the disclosed embodiments. As can be seen in FIG. 2A, when a patient's eye looks straight ahead (i.e., by focusing on the center of screen 102), actuated beam splitter 110 and actuated mirror 112 of headset 100 of FIG. 1 are positioned such that illumination light 202 passes through pupil 204 of globe 220 of the eye and lands on the center region 206 of the retina. As a result, ophthalmic imaging modalities 104 are aligned with and focused on the center region 206 of the retina to capture images of the center region 206.

FIG. 2B shows an exemplary process of aligning the ophthalmic imaging modalities 104 with a peripheral retina region of the fundus in accordance with the disclosed embodiments. As can be seen in FIG. 2B, when the patient's eye looks downward (e.g., when the patient's gaze is attracted to something interesting on a bottom portion of screen 102), the rotation of the globe causes pupil 206 to also move to a new position below the original pupil position in FIG. 2A. As described above, actuated beam splitter 110 and actuated mirror 112 are then automatically repositioned based on the newly determined location of pupil 204 to again guide illumination light 210 through pupil 204 and illustrate a peripheral retina region 212 center region 206. As a result, ophthalmic imaging modalities 104 can now access peripheral retina region 212 to capture images of the peripheral retina region 212.

As globe 220 moves around following the video presentation on the screen, ophthalmic imaging modalities 104 continue to access different parts of the retinal periphery and capture images of different peripheral retina regions. Eventually, at the end of a given ophthalmic imaging process, images including both central and peripheral retina regions are obtained, and widefield OCTs and fundus images can be subsequently reconstructed. Research has shown the advantages of widefield OCT for diagnosis and progression monitoring of ocular diseases, such as diabetic retinopathy (DR), can predominantly affect the peripheral vascular region that are not visible in typical macular OCTs.

Figure 3:
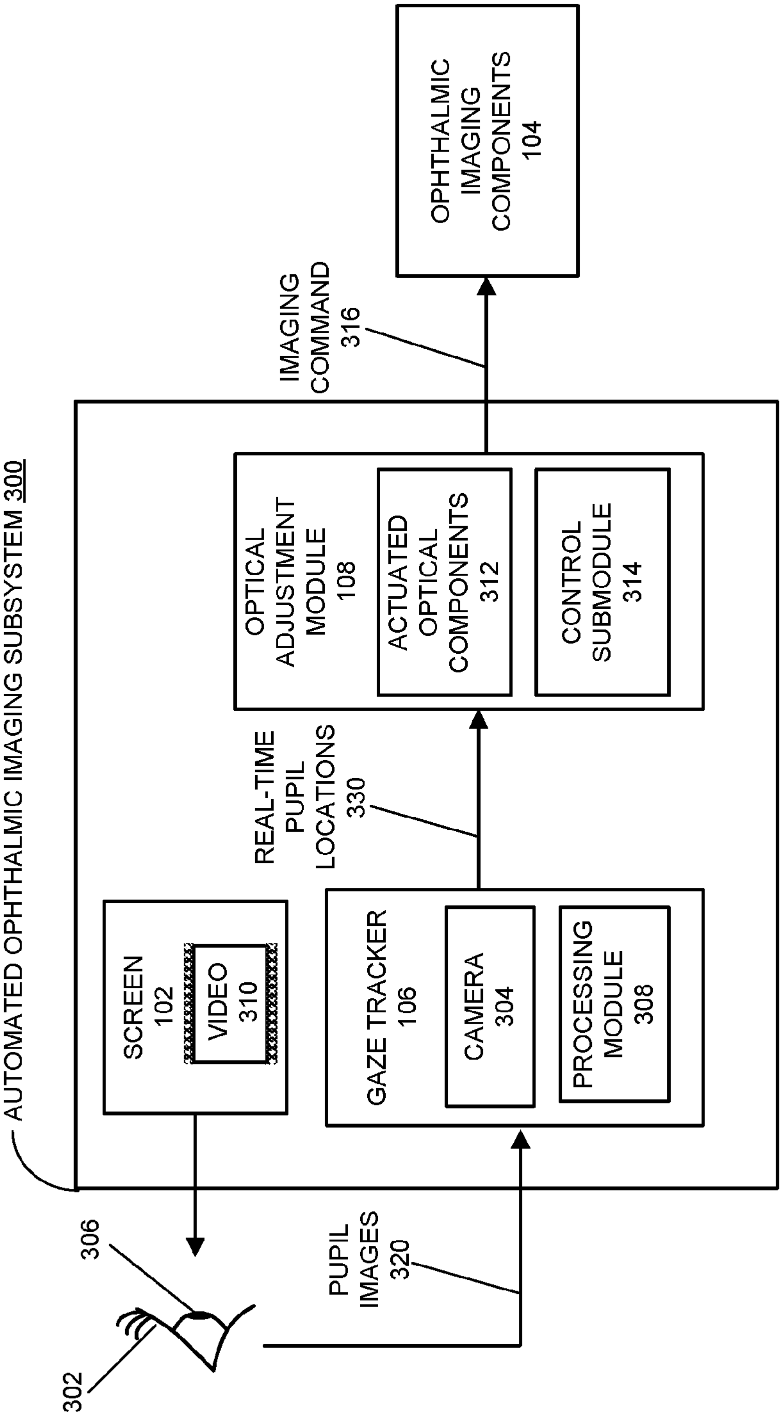
FIG. 3 shows a block diagram of the automated ophthalmic imaging subsystem within the disclosed ophthalmic imaging headset in accordance with the disclosed embodiments.

FIG. 3 shows a block diagram of an automated ophthalmic imaging subsystem 300 within ophthalmic imaging headset 100 in accordance with the disclosed embodiments. Note that FIG. 3 should be understood in conjunction with ophthalmic imaging headset 100 of FIG. 1.

As can be seen in FIG. 3, automated ophthalmic imaging subsystem 300 of ophthalmic imaging headset 100 can include screen 102, which displays a specially-selected entertainment video 310 (or alternatively a sequence of images) that attracts the patient's attention and guides patient's eyes 302 to move in different directions. Automated ophthalmic imaging subsystem 300 also includes gaze tracker 106, which is composed of a camera 304 for taking high resolution images 320 of one or both of patient's eyes 302 including one or both pupils 306, and a gaze processing module 308 configured to determine real-time positions of one or both pupils 306 based on received pupil images 320 as the patient watches the video 310 on screen 102 during a given ophthalmic imaging period. Note that gaze processing module 308 can be implemented with one or more IC chips containing gaze-processing programs. As a result, gaze tracker 106 outputs one or both real-time pupil locations 330 of one or both pupils 306 of patient's eyes 302. While not shown, gaze tracker 106 can additionally include an illuminator configured to project certain patterns over pupils 306, and hence the received pupil images 320 would also include the reflected patterns.

Subsystem 300 additionally includes optical adjustment module 108 coupled to gaze tracker 106 and configured to automatically realign/refocus ophthalmic imaging modalities 104 to maintain optical access to different regions of the fundus based on the received real-time pupil locations 330. Note that optical adjustment module 108 further includes actuated optical components 312, such as actuated beam splitter 110 and actuated mirror 112 shown in FIG. 1, wherein these actuated optical components 312 are typically mounted on actuators such as piezoelectric actuators. Optical adjustment module 108 additionally includes a control submodule 314 coupled to these actuators, which is configured to convert the real-time pupil locations 330 to control signals for the actuators. Hence, the outputs of the control submodule 314 drive the actuators and cause actuated optical components 312 to automatically reposition in response to the changing locations of one or both pupils 306.

As described above in conjunction with FIGS. 2A-2B, repositioning of actuated optical components 312 can direct illumination light to illuminate different peripheral retina regions and at the same time direct the reflected light from different peripheral retina regions back to ophthalmic imaging modalities 104. More specifically, when repositioning of actuated optical components 312 is complete, a new region of the retina is illuminated and the reflected light from the new region is guided toward ophthalmic imaging modalities 104. Note that control submodule 314 can be implemented with one or more IC chips containing pupil-position-conversion programs. Consequently, automated ophthalmic imaging subsystem 300 of ophthalmic imaging headset 100 effectuates a fully automated ophthalmic imaging process for a predetermined imaging duration, without the involvement of an operator/technician or any requirement for the patient to follow examination instructions.

Note that after optical adjustment/realignment to a new part of the retina based on the real-time pupil location 330, control submodule 314 can generate an imaging command 316 to ophthalmic imaging modalities 104, which is coupled to optical adjustment module 108. Upon receiving a new imaging command 316, new OCT scans and fundus images can be automatically captured for the new part of the retina. In some embodiments, after capturing the new OCT scans and fundus images of the new part of the retina, ophthalmic imaging modalities 104 can also be configured to send a notification/signal to the automated ophthalmic imaging subsystem 300, such as to gaze tracker 106, to trigger the gaze tracker to obtain the next real-time pupil location 330. Consequently, as the patient's gaze continues to be guided by video 310 to focus on different parts of the screen 102, gaze tracker 106 continues to generate the real-time pupil locations 330, optical adjustment module 108 continues to realign ophthalmic imaging modalities 104 to maintain optical access to different parts of the retina of patient's eyes 302 based on the real-time pupil locations 330 and generate new imaging commands 316, and ophthalmic imaging modalities 104 continue to capture new OCT scans and fundus images of the different parts of the retina in response to the new imaging commands 316.

Figure 4:
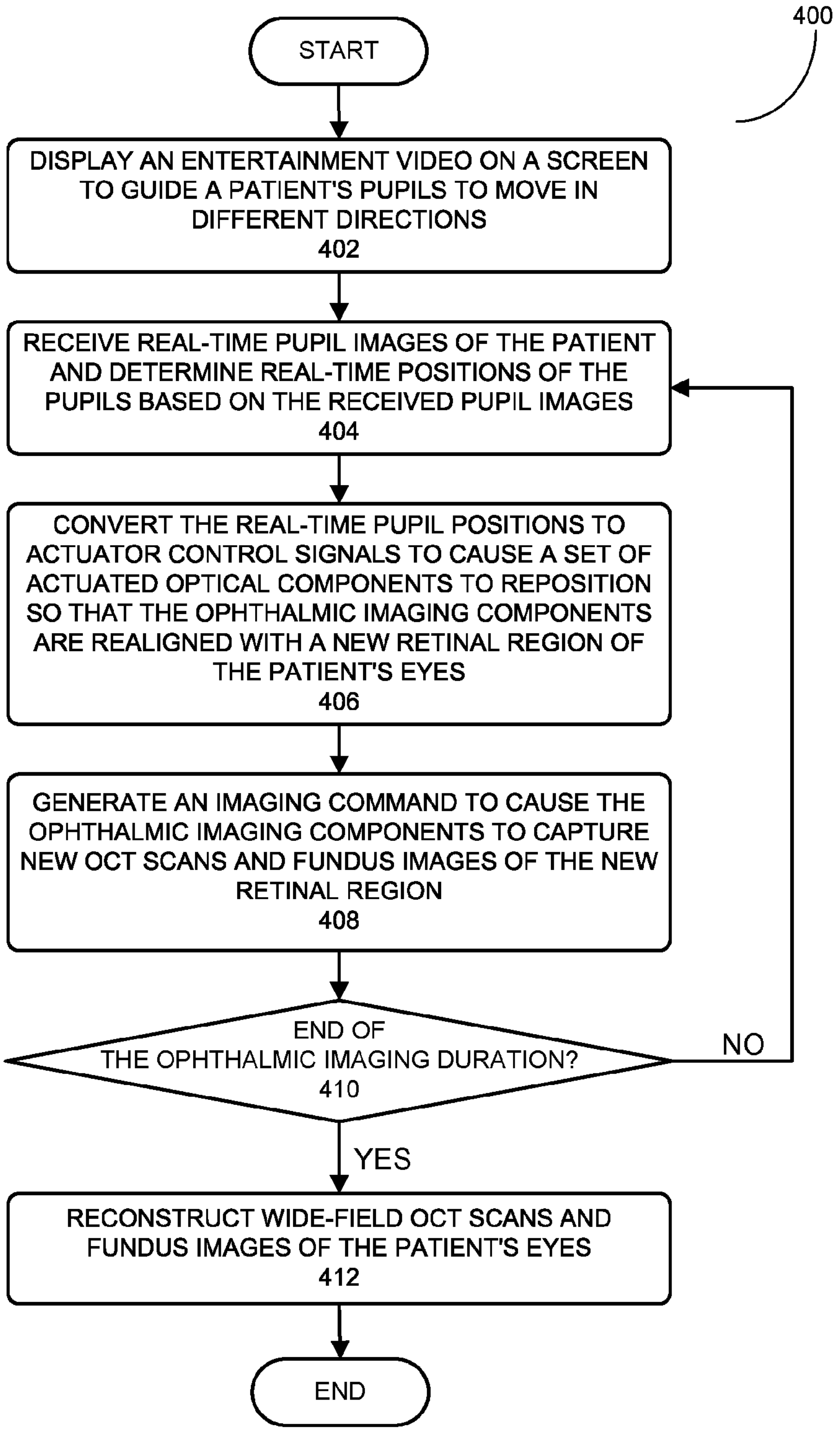
FIG. 4 presents a flowchart illustrating a process for automatically performing widefield OCT scans and fundus imaging on a patient in accordance with the disclosed embodiments.

FIG. 4 presents a flowchart illustrating a process 400 for automatically performing widefield OCT scans and fundus imaging on a patient in accordance with the disclosed embodiments. In one or more embodiments, one or more of the steps in FIG. 4 may be omitted, repeated, and/or performed in a different order. Accordingly, the specific arrangement of steps shown in FIG. 4 should not be construed as limiting the scope of the embodiments.

Process 400 may begin by displaying an entertainment video (or alternatively a sequence of images) on a screen to attract the patient's attention to different parts of the screen, thereby causing patient's pupils to move to focus on different areas of the screen at different times (step 402). In some embodiments, the entertainment video has a predetermined length based on a desired ophthalmic imaging duration. Moreover, the entertainment video should be constructed so that it can hold the patient's attention on each of a set of different locations on the screen for a predetermined time duration to allow sufficient time for the ophthalmic images to be captured on each region of the patient's eyes corresponding to each of the set of different locations on the screen. In some embodiments, the entertainment video can include a VR video or a VR game. Next, one or more real-time pupil images of the patient are received and real-time positions of the pupils are determined based on the received real-time pupil images (step 404). As described above, the one or more real-time pupil images can be captured by a camera within the disclosed gaze tracker within the disclosed ophthalmic imaging headset 100, and the real-time pupil positions can be determined by a processing module with the disclosed gaze tracker.

Next, the real-time pupil positions are converted to actuator control signals to cause a set of actuated optical components to reposition so that the ophthalmic imaging modalities are realigned with a new retinal region of the patient's eyes (step 406). As described above, converting the real-time pupil positions to the actuator control signals can be performed by a control module directed coupled to the actuated optical components. Moreover, after realignment of the ophthalmic imaging modalities, the new retinal region is illuminated and the reflected light from the new retinal region is aligned with the optical axes of the ophthalmic imaging modalities.

Next, an imaging command is generated to cause the ophthalmic imaging modalities to capture new OCT scans and fundus images of the new retinal region (step 408). After step 408, if the end of the ophthalmic imaging duration has not yet been reached (step 410), process 400 returns to step 404 to receive new pupil images and determine new pupil positions, and steps 404-408 repeat.

In some embodiments, the end of the ophthalmic imaging duration coincides with the end of the video presentation on the screen. When process 400 determines that the end of the ophthalmic imaging duration has been reached (e.g., the displayed video has ended), process 400 proceeds to reconstruct widefield OCT scans and fundus images including both central and peripheral retina regions of the patient's eyes (step 412), and process 400 then terminates.

Note that when the disclosed ophthalmic imaging headset 100 is implemented in a VR/3D setup or simply a 2D fully-immersive setup, the intended ophthalmic imaging and ocular exam becomes a relaxing and entertaining process to the patient. Under such an imaging and examination setup, the disclosed ophthalmic imaging headset 100 automatically attracts the patient's full attention, purposefully guides the patent's gaze, and at the same time examines (through ocular images) and evaluates the patient's ophthalmic conditions. Due to the relaxing nature, the duration of the examination/imaging process can be easily extended for more reliable results.

Note that ocular imaging times associated with conventional techniques are typically short (e.g., 1-2 minutes per eye), for a number of reasons. For example, because ocular imaging is often an unpleasant experience, the measurements need to be finished as quickly as possible. In addition, given that the operators involved in performing the imaging are often also responsible for other tasks, they are under pressure to finish the imaging operations quickly, especially during busy clinic days. However, such time constraints on ocular imaging adversely affect the quality of acquired images and confine the location of obtained OCT scans to a central fixation spot (macula). As a result, peripheral retinal imaging is generally not performed in conventional OCT operations at the clinics.

In contrast, the disclosed ophthalmic imaging technology allows the ocular imaging time constraints to be significantly relaxed. Specifically, the imaging duration of the disclosed ophthalmic imaging technology can be set by the length of the entertainment videos or VR games presented to a patient on screen 102. The extended ophthalmic imaging duration opens up new opportunities for thorough and high-quality assessments of central as well as peripheral retina regions of the eyes. The extended ophthalmic imaging duration also allows the imaging quality to be improved through multiple measurements/images to be captured at a given location.

Note that the ophthalmic imaging process and technique using ophthalmic imaging headset 100 is a fully automated process, thereby eliminating the involvement of and need for an expert operator/technician or the requirement for the patient to follow detailed examination instructions. As a result, the disclosed ophthalmic imaging systems and techniques enable independent ophthalmic imaging and examination operations outside clinical settings and in the comfort of the patient's homes. This makes the disclosed ophthalmic imaging technology accessible to conventionally excluded patient groups such as young children, bedridden patients, the elderly, and those with physical or mental disabilities. By making ophthalmic imaging widely accessible, the disclosed technology enables early diagnosis and treatment of ocular diseases, hence preventing many cases of permanent visual impairments. Moreover, because a significant portion of the cost associated with OCT imaging relates to the involvement of experts/technicians, the disclosed ophthalmic imaging technology can significantly reduce the cost of eye care by completely eliminating the involvement of experts/technicians.

Figure 5A:
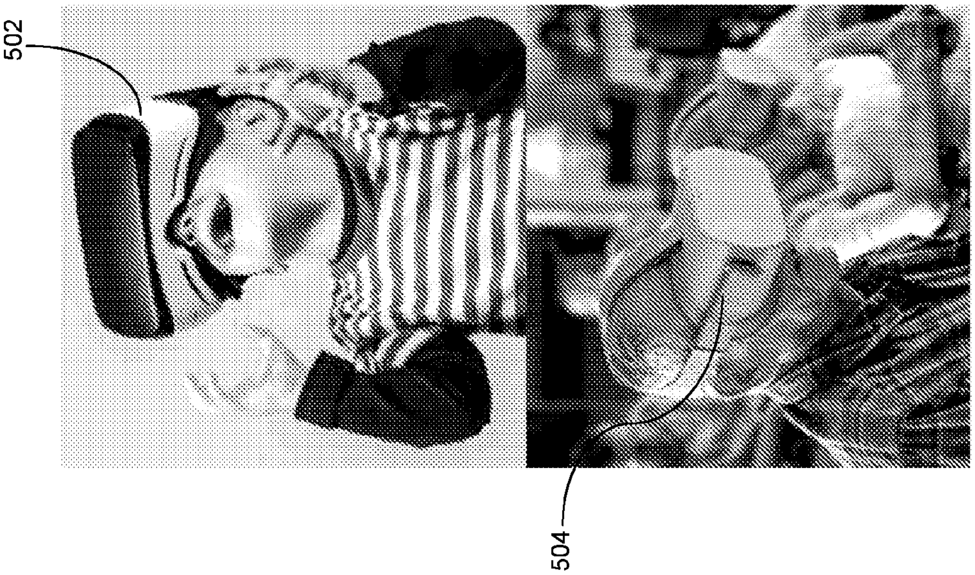
FIG. 5A illustrates two exemplary ocular-imaging/eye examination scenarios using the disclosed ophthalmic imaging headset by two types of targeted patients in accordance with the disclosed embodiments.

FIG. 5A illustrates two exemplary ocular-imaging/eye examination scenarios using the disclosed ophthalmic imaging headset by two types of targeted patients in accordance with the disclosed embodiments. Specifically, the top image in FIG. 5A shows a very young patient wearing a disclosed ophthalmic imaging headset 502 and enjoying an entertaining video or an animation through the headset. The bottom image in FIG. 5A shows an elderly patient, potentially with some disabilities, wearing a disclosed ophthalmic imaging headset 504 and enjoying an entertaining video through the headset. Note that each of the illustrated headsets 502 and 504 in FIG. 5A can be implemented as a VR headset to enhance the visual experiences of the patients and to firmly hold and prolong the patient's attentions.

Figure 5B:
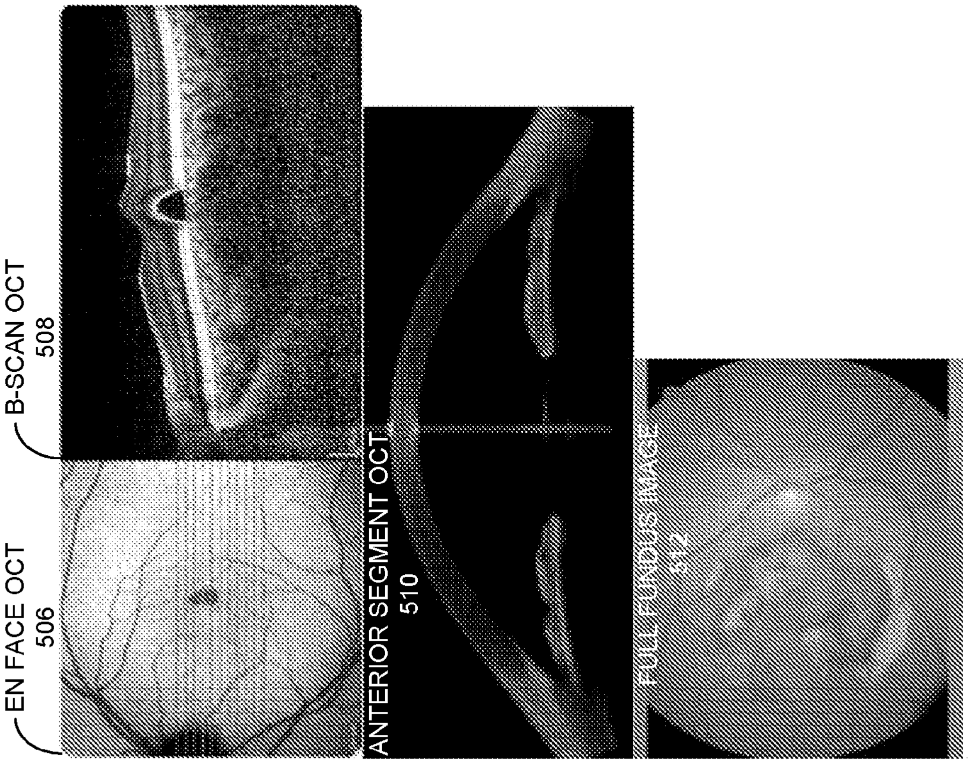
FIG. 5B illustrates different types of ophthalmic images that can be simultaneously and automatically captured by each of the ophthalmic imaging headsets in FIG. 5A during an ocular-imaging/eye examination period in accordance with the disclosed embodiments.

FIG. 5B illustrates different types of ophthalmic images that can be simultaneously and automatically captured by each of the ophthalmic imaging headsets 502 and 504 in FIG. 5A during an ocular-imaging/eye examination period in accordance with the disclosed embodiments. Specifically, the automatically captured ophthalmic images by ophthalmic imaging headsets 502 and 504 can include different types of OCT scans including, but not limited to, En face OCT 506, B-scan OCT 508, and anterior segment OCT 510. Moreover, the ophthalmic images automatically captured by ophthalmic imaging headsets 502 and 504 can include a full fundus image 512 that is reconstructed from many sub-images from both the central and peripheral retina regions.

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A wearable eye examination device, comprising:

one or more ophthalmic imaging modalities that are configured to obtain ophthalmic image data of an eye of a user wearing the wearable eye examination device;

a screen that is configured to display video content to the user wearing the wearable eye examination device;

a gaze tracker that is configured to track a real-time position of a pupil of the user viewing the screen due to changes in a gaze direction of the eye of the user while the video content is displayed;

an optical adjustment module connected to the gaze tracker and configured to align and dynamically guide an optical path of light from a light source associated with the one or more ophthalmic imaging modalities to the real-time position of the pupil based on the gaze direction of the eye of the user while the video content is displayed; and a processing module that is configured to:

cause entertainment video content to be displayed on the screen of the wearable eye examination device during fully-automated ophthalmic imaging, wherein the entertainment video content does not explicitly direct the user to fixate on predetermined locations for the fully-automated ophthalmic imaging;

initiate and continue the fully-automated ophthalmic imaging while the entertainment video content is being displayed on the screen of the wearable eye examination device;

during presentation of the entertainment video content, control the optical adjustment module by repositioning actuated optical components of the optical adjustment module based on the tracked real-time position of the pupil of the user viewing the screen due to changes in the gaze direction of the eye of the user while the entertainment video content continues to be presented, wherein the optical adjustment module is controlled to maintain alignment of the optical path of light from the light source associated with the one or more ophthalmic imaging modalities to the real-time position of the pupil such that the ophthalmic image data from a plurality of different ocular regions of the eye of the user are obtained as the user naturally views the entertainment video content; and reconstruct, from the ophthalmic image data obtained from the plurality of different ocular regions, a composite widefield ophthalmic image that combines the ophthalmic image data obtained from the plurality of different ocular regions upon completion of the entertainment video content.

2. The wearable eye examination device of claim 1, wherein the one or more ophthalmic imaging modalities include at least an optical coherence tomography (OCT) and a fundus imaging module.

3. The wearable eye examination device of claim 1, wherein the screen, when displaying the video, acts as an illumination source for the one or more ophthalmic imaging modalities.

4. The wearable eye examination device of claim 1, wherein the gaze tracker further includes:

a camera for capturing one or more real-time images of the pupil; and the processing module configured to determine the real-time position of the pupil based on the captured real-time images of the pupil.

5. The wearable eye examination device of claim 4, wherein the processing module is further configured to covert the real-time position of the pupil into an actuation signal.

6. The wearable eye examination device of claim 5, wherein the optical adjustment module further includes the actuated optical components coupled between the real-time position of the user's eye and the one or more ophthalmic imaging modalities, and wherein the optical adjustment module is configured to align the region of the user's eye with the one or more ophthalmic imaging modalities by repositioning the actuated optical components based on the actuation signal so that reflected light from the region of the user's eye is aligned with optical axes of the one or more ophthalmic imaging modalities.

7. The wearable eye examination device of claim 6, wherein the one or more actuated optical components include one or both of:

an actuated beam splitter; and an actuated mirror.

8. The wearable eye examination device of claim 7, wherein the actuated beam splitter is positioned between the user's eye and the screen and is configured to transmit a first portion of incident light toward the user's eye and reflect a second portion of the incident light toward the actuated mirror.

9. The wearable eye examination device of claim 6, wherein the processing module is further configured to:

determine the completion of the repositioning of the one or more actuated optical components; and generate an imaging instruction to the one or more ophthalmic imaging modalities.

10. The wearable eye examination device of claim 9, wherein the one or more ophthalmic imaging modalities, upon receiving the imaging instruction, are further configured to capture both OCT scans and fundus images of the region of the user's eye.

11. The wearable eye examination device of claim 1, wherein the region of the user's eye includes:

a central region of the retina; and a peripheral region of the retina.

12. The wearable eye examination device of claim 1, further comprising an image processing module configured to reconstruct widefield OCT scans and fundus images including both central and peripheral retina regions of the patient's eye based on captured OCT scans and fundus images from different regions of the user's eye during an extended ophthalmic imaging period.

13. The wearable eye examination device of claim 1, wherein the wearable eye examination device is implemented as a virtual reality (VR) headset.

14. The wearable eye examination device of claim 13, wherein the wearable eye examination device allows for performing fully-automated ophthalmic imaging on the user over an extended examination period facilitated by the entertainment video content and the comfort of the user wearing the VR headset.

15. The wearable eye examination device of claim 14, wherein the extended examination period facilitates capturing multiple OCT scans and fundus images of multiple regions of the user's eye to improve image qualities of the fully-automated ophthalmic imaging.

16. The wearable eye examination device of claim 1, wherein the wearable eye examination device enables the fully-automated ophthalmic imaging without the involvement of a technician.

17. The wearable eye examination device of claim 1, wherein the wearable eye examination device is implemented as an OCT-fundus dual modality headset.

18. The wearable eye examination device of claim 1, wherein the wearable eye examination device enables the fully-automated ophthalmic imaging without requiring the user's cooperation.

19. A method of performing fully automatic ophthalmic imaging, the method comprising:

displaying entertainment video content on a screen associated with a wearable device to initiate fully-automated ophthalmic imaging of a pupil of a patient wearing the wearable device, wherein the entertainment video content does not explicitly direct the user to fixate on predetermined locations for the fully-automated ophthalmic imaging;

concurrently capturing ophthalmic images of one or more retinal regions of the pupil using one or more ophthalmic imaging modalities that are configured to obtain ophthalmic image data of an eye of the patient wearing the wearable device while the entertainment video content is being displayed;

determining, using a gaze tracker, a real-time position of the pupil of the patient viewing the screen due to changes in a gaze direction of the eye while the entertainment video content is being displayed;

during presentation of the entertainment video content, controlling an optical adjustment module associated with the wearable device by converting the real-time position of the pupil of the patient into a control signal and repositioning actuated optical components of the optical adjustment module based on the control signal, wherein the optical adjustment module is controlled to maintain alignment of an optical path of light from a light source associated with the one or more ophthalmic imaging modalities to the real-time position of the pupil such that the ophthalmic image data from a plurality of different ocular regions of the eye of the patient are obtained as the patient naturally views the entertainment video content; and reconstructing, from the ophthalmic image data obtained from the plurality of different ocular regions, a composite widefield ophthalmic image that combines the ophthalmic image data obtained from the plurality of different ocular regions upon completion of the entertainment video content.

20. The method of claim 19, wherein the one or more ophthalmic imaging modalities include at least an optical coherence tomography (OCT) and a fundus imaging module.

21. The method of claim 19, wherein determining the real-time position of the pupil of the patient includes:

capturing one or more real-time images of the pupil of the patient; and determining the real-time position of the pupil of the patient based on the captured real-time images.

22. The method of claim 19, wherein the repositioning of the actuated optical components of the optical adjustment module further comprises repositioning one or more actuated optical components such that reflected light from a new retinal region of the eye of the patient is aligned with optical axes of the one or more ophthalmic imaging modalities.

23. The method of claim 22, wherein prior to capturing the ophthalmic image data, the method further comprises:

determining completion of the repositioning of the one or more actuated optical components; and generating an imaging instruction to the one or more ophthalmic imaging modalities to trigger imaging functions of the one or more ophthalmic imaging modalities.

24. The method of claim 19, wherein the method further comprises extending a duration of a session of the fully-automated ophthalmic imaging by displaying second entertainment video content on the screen.

25. The method of claim 19, wherein the fully-automated ophthalmic imaging is performed without the involvement of a technician.

26. The method of claim 19, wherein the fully-automated ophthalmic imaging is performed without requiring the patient's cooperation.

27. The method of claim 19, wherein the fully-automated ophthalmic imaging is performed at a patient's home.

28. An ophthalmic imaging headset, comprising:

one or more ophthalmic imaging modalities that are configured to obtain ophthalmic image data of an eye of a user wearing the headset;

a screen that is configured to display video content to the user wearing the headset to catch and hold the user's attention to one or more locations on the screen;

an optical adjustment module that is configured to maintain optical access of the one or more ophthalmic imaging modalities to one or more regions of interest of one or both eyes of the user by aligning and dynamically guiding an optical path of light from a light source associated with the one or more ophthalmic imaging modalities to a real-time position of a pupil of the user viewing the screen while the video content is displayed; and a processing module that is configured to:

cause entertainment video content to be displayed on the screen of the headset during fully-automated ophthalmic imaging, wherein the entertainment video content does not explicitly direct the user to fixate on predetermined locations for the fully-automated ophthalmic imaging;

initiate and continue the fully-automated ophthalmic imaging while the entertainment video content is being displayed on the screen of the headset;

during presentation of the entertainment video content, control the optical adjustment module by repositioning actuated optical components of the optical adjustment module while the entertainment video content continues to be presented, wherein the optical adjustment module is controlled to maintain alignment of the optical path of light from the light source associated with the one or more ophthalmic imaging modalities to the real-time position of the pupil such that the ophthalmic image data from a plurality of different ocular regions of the eye of the user are obtained as the user naturally views the entertainment video content; and reconstruct, from the ophthalmic image data obtained from the plurality of different ocular regions, a composite widefield ophthalmic image that combines the ophthalmic image data obtained from the plurality of different ocular regions upon completion of the entertainment video content.

29. The ophthalmic imaging headset of claim 28, wherein the one or more ophthalmic imaging modalities include at least an optical coherence tomography (OCT) for capturing posterior segment images of the one or both eyes of the user and a fundus imaging module for capturing retinal images of the one or both eyes of the user.

30. The ophthalmic imaging headset of claim 28, further comprising a gaze tracker that is configured to track a real-time position of the pupil of the user viewing the screen due to changes in a gaze direction of the eye of the user while the entertainment video content is displayed.

31. The ophthalmic imaging headset of claim 30, wherein the optical adjustment module is configured to maintain the optical the alignment of the optical path of light from the light source associated with the one or more ophthalmic imaging modalities to the real-time position of the pupil.

32. The ophthalmic imaging headset of claim 28, wherein the optical adjustment module includes one or both of:

an actuated beam splitter; and an actuated mirror.

33. The ophthalmic imaging headset of claim 28, wherein the optical adjustment module includes a stationary beam splitter.

* * * * *